United States Patent
Hack et al.

[11] Patent Number: 5,897,314
[45] Date of Patent: Apr. 27, 1999

[54] MEDICAL OR DENTAL LASER INSTRUMENT, ESPECIALLY FOR DENTAL ROOT CANAL TREATMENTS

[75] Inventors: Alexander Hack; Ursula Schmitt, both of Biberach, Germany

[73] Assignee: Kaltenbach & Voigt GmbH & Co., Biberach, Germany

[21] Appl. No.: 08/919,435

[22] Filed: Aug. 27, 1997

[30] Foreign Application Priority Data

Sep. 6, 1996 [DE] Germany ............................ 196 36 265
Oct. 2, 1996 [DE] Germany ............................ 196 40 803

[51] Int. Cl.[6] ...................................................... A61C 1/00
[52] U.S. Cl. ................................ 433/29; 433/224; 606/16
[58] Field of Search ............................... 433/29, 126, 127, 433/128, 224; 606/16

[56] References Cited

U.S. PATENT DOCUMENTS

| | | | |
|---|---|---|---|
| 4,671,273 | 6/1987 | Lindsey | 128/303.1 |
| 4,826,431 | 5/1989 | Fujimura et al. | 433/29 |
| 5,300,067 | 4/1994 | Nakajima et al. | 606/16 |
| 5,364,391 | 11/1994 | Konwitz | 606/16 |
| 5,388,987 | 2/1995 | Badoz et al. | 433/29 |

FOREIGN PATENT DOCUMENTS

| | | |
|---|---|---|
| 0 375 578 | 6/1990 | European Pat. Off. . |
| 0 413 660 | 2/1991 | European Pat. Off. . |
| 0 487435 | 5/1992 | European Pat. Off. . |
| 4038809 | 12/1990 | Germany . |
| 4233744 | 4/1994 | Germany . |
| 5344982 | 12/1993 | Japan ...................................... 433/29 |
| WO 85/05262 | 12/1985 | WIPO . |

*Primary Examiner*—John J. Wilson
*Attorney, Agent, or Firm*—Scully, Scott, Murphy & Presser

[57] ABSTRACT

In a medical or dental laser instrument (1), especially for tooth root canal treatments, having a preferably rod-shaped hand piece (2), a connection part (3) by means of which the hand piece (2) can be connected to a supply line (4), a first light guide (5) that extends longitudinally through the supply line (4) and the connection part (3) to the hand piece (2), a second light guide (7) arranged in the front end region of the laser instrument, the rear end of the second light guide (7) being arranged coaxially with respect to the front end of the first light guide (5), and a coupling device (8) for coupling the laser light bundle leaving the first light guide (5) to the second light guide (7), the said second light guide (7) has a larger numerical aperture than the first light guide (5).

17 Claims, 2 Drawing Sheets

Fig. 2
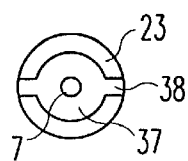
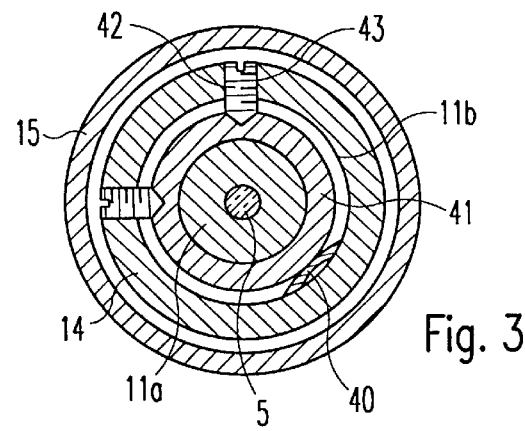
Fig. 3

Fig. 11

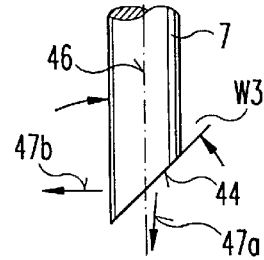

MEDICAL OR DENTAL LASER INSTRUMENT, ESPECIALLY FOR DENTAL ROOT CANAL TREATMENTS

BACKGROUND OF THE INVENTION

1. Field of the Invention

The invention relates to a medical or dental laser instrument, especially for tooth root canal treatments.

2. Discussion of the Prior Art

A laser instrument of this type is generally known and is described for example in DE 40 38 809 C1 and in DE 42 33 744 A1.

The laser instrument according to DE 40 38 809 C1 has a second light guide at its front end that is laterally spaced from the laser instrument. Several second light guides of different cross-sectional size are associated with the laser instrument, one of which second light guides has such a small diameter that it is suitable for use in dental root canal treatment. In this known arrangement the coupling into the second light guide is effected by means of a prism that reflects the laser beams back sideways into the second light guide. An axially adjustable lens is arranged between the first light guide and the prism, the axial adjustment of the lens enabling the cross-sectional size of the laser light bundle to be matched to the respective cross-sectional size of the second light guide.

DE 42 33 744 A1 discloses a laser instrument with three light guides arranged in succession in the longitudinal direction, between each of which guides is arranged a coupling device with two lenses. In this known arrangement the middle light guide is curved. In this way it is possible to arrange the front light guide at an angle to the mid axis of the laser instrument without having to provide a deflecting device for the laser light bundle. The ends of the light guides in each case lie coaxially relative to one another in the region of the coupling devices.

The utility of a laser instrument depends among other things on the output of the laser beam bundle leaving the free end of the second light guide. In this connection an essential requirement is to guide the laser beam bundle with as little loss as possible in the light guides and to couple it to the coupling devices. In order to achieve this the numerical aperture of the light guides must not fall below a specific value. Failing this the highest possible degree of total reflection in the light guides will not be ensured as soon as the opening angle of the light cone to be transmitted exceeds the limiting angle of the light guide, which corresponds to the numerical aperture of the light guide.

SUMMARY OF THE INVENTION

The object of the invention is to design a laser instrument of the type described at the beginning in such a way that the laser light bundle can be coupled without loss or with as little loss as possible into the second light guide, while ensuring a compact and/or short design and construction.

In the arrangement according to the invention the second light guide has a larger numerical aperture than the first light guide. In this way the second light guide is able to receive a convergent laser light bundle of relatively large acute angle, without correspondingly losing much light. A low loss or loss-free coupling can thus be substantially improved while ensuring a short and compact construction.

The problem that the invention aims to solve occurs particularly if the laser light bundle has to be coupled into a second light guide whose cross-sectional size is smaller than the cross-sectional size of the first light guide. If one does not wish to increase the structural length or the distance of the rear end face of the second light guide from the coupling device, the cross-sectional reduction in size of the second light guide inevitably leads to a corresponding coupling loss. In the arrangement according to the invention on the other hand, the laser light bundle can be coupled in a low loss or loss-free manner without having to increase the structural length or relevant distance.

The laser instrument according to the invention is thus particularly suitable for dental root canal treatments in which a second light guide of extremely small cross-sectional size is absolutely essential since otherwise a root treatment is not possible.

A further object of the invention is to improve the adaptability of the laser instrument to different treatment sites.

In a particular arrangement according to the invention the second flexible light guide is stabilised by a small tube surrounding the light guide and projecting from the laser instrument, the said small tube being formed of a plastically deformable material of such a strength that it can be bent with the operating hand. It is thus possible in a simple way to alter the shape of the small tube and adapt it to the respective treatment site. This represents a substantial simplification since it is not necessary to provide several second light guides of different shapes, which would have to be changed in each case as appropriate and would involve considerable expense and effort.

The object of the invention is furthermore to improve the efficiency of a laser instrument of the type disclosed the preamble of claim 10.

In an improved and more efficient laser instrument, the arrangement is particularly suitable for a canal treatment, for example a dental root canal treatment. The essential advantage of this arrangement is that the light guide is effective all the way round on account of its rotatability. This is of great advantage particularly when treating tooth root canals, since, as is known, root canals are curved and therefore inaccessible, with the result that treatment is difficult and often cannot be performed at all the necessary sites, which can severely affect the quality of the dental treatment. With the arrangement according to the invention on the other hand, an all-round action in every deep position of the light guide in the root canal is ensured.

The object of the invention is furthermore to improve the adaptability of a laser instrument of the type described.

This object is achieved by the features of claim 13.

In this arrangement according to the invention the holders, in each case containing a light guide, can be coupled on the one hand in a user-friendly manner and on the other hand reliably to the laser instrument by means of a quick-action connection. The person carrying out the treatment can thus couple any desired light guide to the laser instrument simply and quickly and without having to pay particular attention. The quick-action connection is preferably designed so that it ensures an accurate axial positioning of the holder, which is important having regard to a loss-free or lowest possible loss coupling of the laser beam bundle. In this connection it is particularly advantageous to design the quick-action connection so that in each case it presses the holder against a specific striking or reference surface and thereby effects an accurate positioning.

The subclaims contain features that further improve the coupling of the laser light bundle and the mounting of the light guide and also provide compact and inexpensive arrangements that can advantageously be integrated into the small spacial conditions of a hand-held laser instrument.

BRIEF DESCRIPTION OF THE DRAWINGS

The invention and further advantages achievable thereby will be described in more detail hereinafter with reference to preferred embodiments and with the aid of the accompanying drawings, in which:

FIG. 2 is a rear view of a holding shank for a second light guide;

FIG. 3 shows the partial section III—III of FIG. 1;

FIGS. 4 to 12 show different forms of the free end of a light guide treatment section.

DETAILED DESCRIPTION OF PREFERRED EMBODIMENTS

Figure 1:
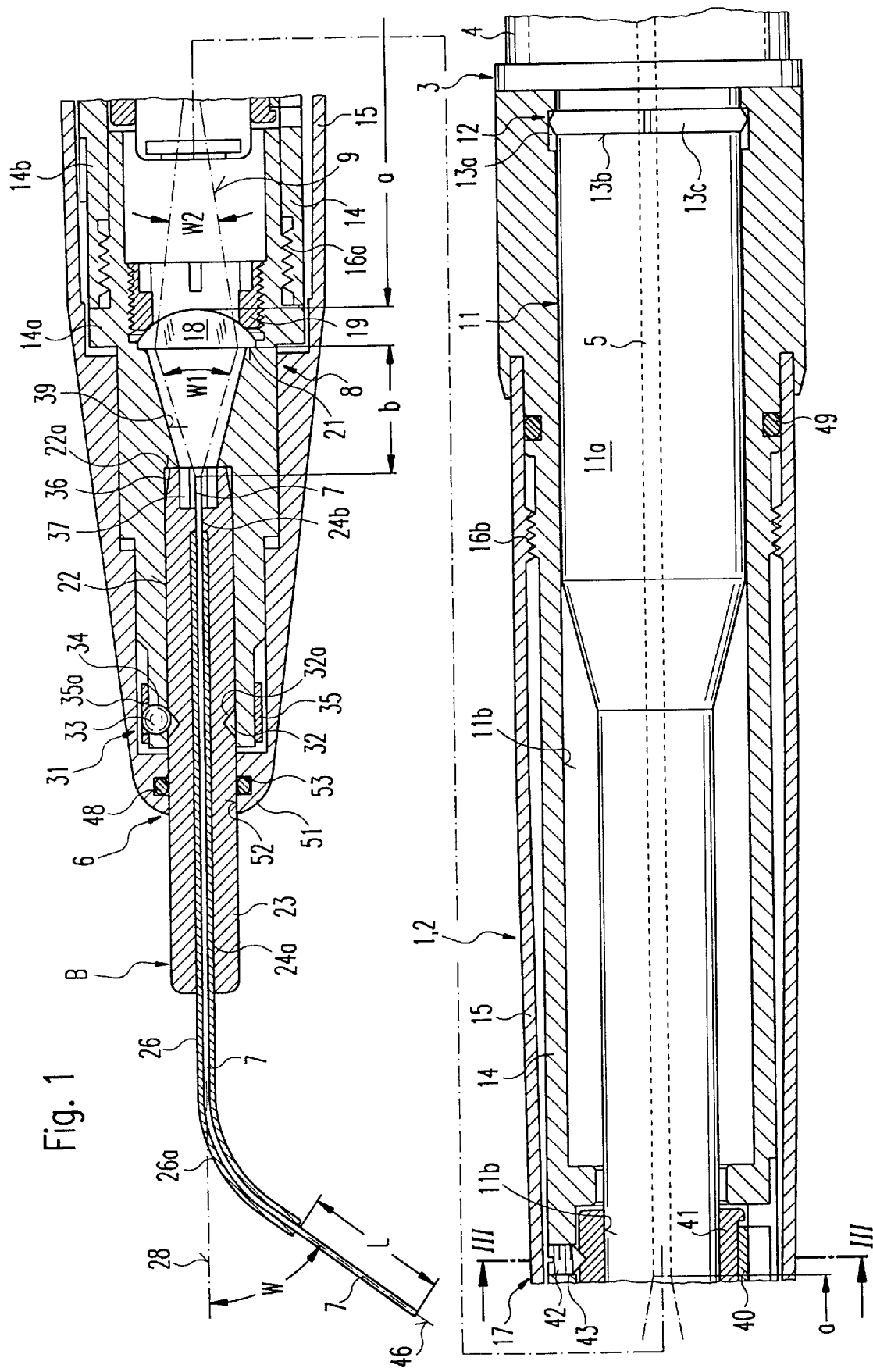
FIG. 1 is an axial section through a laser instrument according to the invention.

The main parts of the laser instrument 1 are a preferably rectilinear rod-shaped hand piece 2, a connection piece 3 to which the hand piece 2 can be connected and to which a flexible supply line 4 can be joined, in which latter a first light guide 5 extends through the connection piece 3 into the hand piece 2, a holding device 6 formed by a quick-action connection for a second light guide 7 that projects with a treatment section from the hand piece 2, and a coupling device 8 by means of which the laser light bundle 9 leaving the first light guide 5 can be coupled into the rear end of the second light guide 7.

A plug-in/rotational coupling 11 having a coupling pin 11a and a coupling recess 11b accommodating the latter is provided for releasably connecting the hand piece 2 to the connection piece 3. In the present arrangement the coupling pin 11a is a cylindrical or stepped cylindrical coupling pin that is arranged on the connection piece 3 and projects therefrom. The coupling recess 11b is arranged in the rear end region of the hand piece 2. A releasable locking device 12 is associated with the plug-in/rotational coupling 11, which device can preferably be manually pressed and thus automatically engage with the coupling and can also be disengaged by pressing. Such a locking device 12 is preferably formed by an annular groove 13a forming a locking edge in the external circumferential surface of the coupling pin 11a or in the internal circumferential surface of the coupling recess 11b, in which a spring element, for example a spring washer 13c arranged in an oppositely facing annular groove or engaging in its effective position under the action of a spring-loaded ball, can be formed. On account of the presence of an annular groove 13a as locking element, the locking device 12 is able to releasably engage in every rotational position of the hand piece 2.

The hand piece 2 consists of a rod-shaped inner part 14 accommodating the optical elements and an outer part in the form of a gripping sleeve 15 surrounding the inner part 14, the gripping sleeve tapering to a truncated conical shape in its front end region. The gripping sleeve 15 and the inner part 14 are radially centered in the front end region by a fit 16a and are screwed together in their front end region by a threaded engagement 16b. The inner part 14 has an axially continuous channel of varying cross-sectional dimensions. In the rear half this channel forms the coupling recess 11b into which the cylindrical coupling pin 11a is inserted, the pin having a front tapering coupling pin section. An adjustment device 17 is arranged in the inner part 14 in the front end region of the coupling pin 11a, which device enables the position of the coupling pin 11a to be radially adjusted and fixed in the inner part 14. The first light guide 5 is mounted in a continuous bore within the coupling pin 11a, the said guide terminating at a distance behind the free end of the coupling pin 11a and thus being protected against any damage. A lens 18 is centrically arranged in a cylindrical channel section at a distance a forward from the front end of the first light guide 5, the lens being clamped against a shoulder surface 21 by means of a sleeve nut 19 screwed into an internal thread of the channel section. The second light guide 7 is held in position in the internal part 14 at a distance b forward from the lens 18 by means of the holding device 6.

The holding device 6 for the second light guide 7 comprises a plurality of holding elements. A cylindrical stepped bore 22 is arranged in the front end region of the inner part 14, into which bore a cylindrical holding shank 23 of appropriately large cross-section can be inserted with a small degree of play from the front as far as the shoulder surface 22a of the stepped bore. The holding shank 23 also has a coaxial cylindrical stepped bore whose larger stepped bore section 24a extends forwardly over the greater part of the length of the holding shank 23, so that the smaller stepped bore section 24b is arranged in the rear part of the holding shank. The section 24b corresponds as regards its cross-sectional size to the cross-sectional size of the second light guide 7. A supporting tube 26 is inserted into the larger stepped bore section 24a, the external cross-section of the supporting tube being adapted to the cross-sectional size of the stepped bore section 24a and its internal cross-section being adapted to the cross-sectional size of the second light guide 7. The supporting tube 26 projects beyond the holding shank 23 by a considerable extent of some 15 to 20 mm in the present arrangement. The second light guide 7 also projects a considerable extent beyond the supporting tube 26, in this case by about 28 mm. The supporting tube 26 and the second light guide 7 may, depending on the particular use, be rectilinear or may bend sideways, as shown in FIG. 1. The arcuate section 26a of this curvature is situated roughly in the middle in the projecting region of the supporting tube 26. In such an arrangement the light guide 7 consists of a manually plastically flexible material that can be bent manually into any desired curved shape. In the present arrangement the laterally or angularly bent section of the supporting tube 26 and of the light guide 7 form a forwardly open angle W of about 70° with the longitudinal mid axis 28 of the laser instrument 1. In the present embodiment the external diameter of the supporting tube 26 is about 1 mm.

The length L by which the light guide 7 forming the treatment section projects beyond the supporting tube 26 may vary depending on different treatment cases.

The light guide 7, the supporting tube 26 and the holding shank 23 form a structural unit whose parts are rigidly connected to one another, for example by bonding, to form a structural part B. In order to secure the holding shank 23 in its plug-in connection, a manually pressurable locking device 31 is provided that automatically elastically locks and can be released by manual pressure. One of the elements of the locking device is an annular groove 32 in the external circumferential surface of the holding shank 23 or in the internal circumferential surface of the inner part 14, into which the associated locking element 33 may penetrate and engage under the action of a spring. In the present arrangement the annular groove 32 is arranged in the external circumferential surface of the holding shank 23 and the locking element 33 is formed by a ball sitting with a degree of play in a radial hole 34 in the inner part 14. The associated spring element is an annular spring or circlip that presses the locking element 33 radially inwardly into the locking recess. In order that the ball does not fall out of the hole 34 when the holding shank 23 is withdrawn, the hole 34 tapers at its inner end so that the ball can engage by a necessary amount in the annular groove 32, though the ball is prevented by positive engagement from completely leaving the hole. In order to save radial structural size, in the annular spring 35 a hole 35a is provided for the ball, in which the latter may engage. In this way the annular spring 35 is also safeguarded against any unintentional axial displacement.

Preferably the arrangement is such that the locking device 31 under pressure axially secures the structural part denoted by B and also positions it in the circumferential direction. The former objective is achieved if the annular groove 32 has a rearwardly inclined flank 32a against which the ball presses radially inwards and thereby produces an axially rearwardly directed force component that presses the holding shank 23 and thus the structural part B against the shoulder 21 or reference surface. In order to facilitate the introduction of the holding shank 23, the latter has at its rear end a slight conical introduction surface 36 on which the ball can easily roll.

The rear end of the second light guide 7 is located in a rear recess 37 of the holding shank 23, the rear end of the light guide 7 being forwardly displaced relative to the rear end of the holding shank 23 and thus being arranged deep and protected. In order to be able to measure and control more accurately the position of the rear end of the light guide 7, the holding shank 23 has at its rear end a diametrical slit 38 through which the rear end of the light guide 7 is accessible for measurement or for checking.

A forwardly tapering truncated conical channel section 39 is arranged in the region between the shoulder surfaces 21 and 22a, whose forwardly converging shape enables the shoulder surface 22a to be formed, even though the cylindrical stepped bore 22 is of smaller cross-sectional size than that of the channel section accommodating the lens 18.

In order to simplify the construction it is advantageous to form the inner part 14 of two parts that can be joined to one another. In the present arrangement a front inner part section 14a and a rear inner part section 14b are provided that are screwed together. In the present arrangement also the dividing groove between these two parts is situated in the region of the lens 18 or sleeve nut 19, thereby facilitating their assembly and dismantling.

The adjustment device 17 has an adjustment ring 41 arranged with a degree of radial play in the inner part 18, which adjustment ring forms a front carrying section of the coupling recess 11b in which the coupling pin 11a sits with a small degree of play. The adjustment ring 41 can be radially adjusted on all sides and can be secured in the relevant adjustment position. A plurality of adjustment screws 42 arranged distributed around the circumference may serve for this purpose, which are screwed into corresponding radial threaded holes 43 in the inner part 14 and can be pressed from outside against the adjustment ring 41, the said adjustment ring 41 preferably being provided with small, optionally conical recesses in which the adjustment screws 42 with conical tips can engage. In the present arrangement only two adjustment screws 42 with associated threaded holes 43 are provided, whose mid axes enclose roughly a right angle, a spring element 44 being arranged between the adjustment ring 41 and the inner part 14 opposite the adjustment screw 42 and elastically forcing the adjustment ring 41 against the adjustment screw 42. The spring element 44 may be formed for example by a leaf spring.

The first light guide 5 is a conventional light guide, with flexible supply leads 4, in the form of a fibre having a diameter of about 500 µm to 800 µm and a numerical aperture of less than 0.2, preferably between 0.13 and 0.18.

The second light guide 7 has a smaller cross-sectional size than the first light guide 5, this smaller cross-section having a diameter of about 200 µm to 500 µm. This light guide 7 is consequently a smaller fibre, though the numerical aperture is greater than 0.2 and is preferably 0.26 to 0.35. The cross-sectional sizes of the fibres 5, 7 and their numerical apertures are thus in a reciprocal relationship to one another. This arrangement enables laser light to be uncoupled from a large fibre into a small fibre without thereby losing correspondingly much light on account of the cross-sectional reduction of the fibres 5, 7. The laser light bundle focussed by the lens 18 can thus enclose an angle W1 that is correspondingly larger than the divergent angle W2 of the laser light bundle leaving the first light guide 5. It should also be borne in mind that the distance b can be kept relatively small. It is accordingly found that the laser light can be transmitted more efficiently, and at the same time it is possible to adapt the light guide 7 to small cross-sectional dimensions.

The free end of the second light guide 7 can have various shapes, which in each case permit different types of treatment or are effective in varying degrees.

Figure 4:
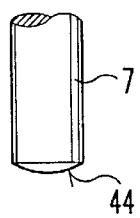
Figure 5:
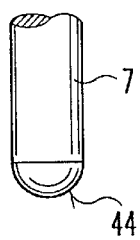

In the arrangements according to FIGS. 4 and 5 the cylindrical light guide 7 has a spherical front face 44, according to FIG. 4 a flat cone being provided and according to FIG. 5 a hemispherical cone being provided.

Figure 6:
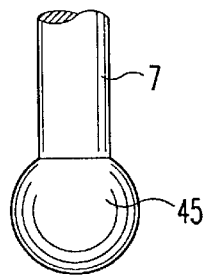

According to FIG. 6 a spherical enlargement 45 is provided on the free end of the cylindrical light guide 7.

Figure 7:
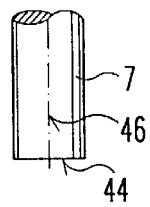

According to FIG. 7 the front face 44 is formed flat and at right angles to the longitudinal mid axis 46 of the light guide 7.

Figure 8:
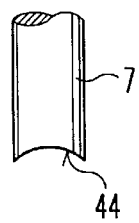

In the arrangement according to FIG. 8 the front face 44 is formed concavely, and is preferably round. In this connection the front face may have a curvature that runs in a transverse and continuously prismatic manner or that is spherical.

Figure 9:
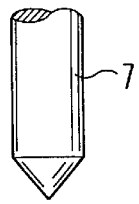
Figure 10:
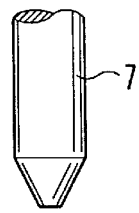

According to FIGS. 9 and 10 the free end of the cylindrical light guide 7 has a conical tip (FIG. 9) or a truncated conical tip (FIG. 10).

In the arrangement according to FIG. 11 an axial outlet 47a and/or a lateral outlet 47b are provided for the laser light. In this arrangement the free end of the light guide 7 has a preferably flat and inclined front face 44 whose angle W3 may vary with respect to the longitudinal mid axis 46. Depending on the size of this angle and having regard to the physical and optical circumstances, there is a partial or total reflection to the opposite side and thus to the lateral light outlet 47b. This is of great advantage for carrying out treatment in a canal, especially in a tooth root canal, since the effectiveness of the light guide 7 is directed axially, axially and laterally, or laterally. In this way it is possible to treat directly and/or cut away the canal wall, as is conventional in a laser irradiation.

Figure 12:
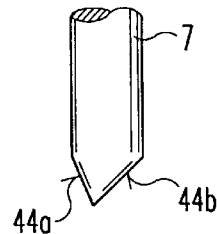

A further variant is shown in FIG. 12, in which wedge-shaped front face parts 44a, 44b are provided on both sides, which may enclose an obtuse or acute angle and/or may be symmetrically or eccentrically arranged, as shown in FIG. 12.

It is furthermore of advantage to mount the second light guide 7 rotatably and to drive it by means of a rotational drive during the functional operation of the laser instrument 1. Such an arrangement is particularly suitable for a light guide 7 having an at least partial or completely lateral or all-round light outlet 47b. The rotational drive (not shown) may engage the light guide 7 directly or indirectly. In the present arrangement the rotational drive could engage the holding shank 23.

It is also advantageous to supply a treatment fluid, for example water and/or a water/air mixture or spray, to the treatment site. This can be achieved by means of one or two channels running longitudinally in the hand piece, as is known per se. In the present arrangement the at least one channel could be arranged in the region of the holding shank 23 or in the region of the supporting tube 26 and could be formed for example by a groove in each case on the inner circumferential surface, so that the treatment fluid leaves the front end of the holding shank 23 or of the supporting tube 26. In the first case the treatment fluid may run along the supporting tube 26 and the treatment section of the light guide 7, and in the second case may run along the treatment section of the light guide 7 to the treatment site.

It is advantageous to allocate a plurality of exchangeable structural parts B to the laser instrument 1 that differ from one another, for example as regards the length 1 of the treatment section of the second light guide and/or its cross-sectional size and/or the flexibility of the supporting tube.

As can be seen from FIG. 1, the gripping sleeve 15 seals the inner part 14 by means of sealing rings 48, 49 arranged at the front end and at the rear end. In the present arrangement the gripping sleeve 15 overlaps the front end of the inner part 14 in the manner of a cap, the front end of the cap 51 having a coaxial bore 52 whose cross-sectional size is adapted to the cross-sectional size of the holding shank 23 and is sealed by the associated sealing ring 48, which may be arranged in an annular groove 53 in the cap 51.

For a prescribed treatment for purposes of irradiation and/or to cut away tissue, it is advantageous to use a Er:YAG-laser that is guided from a control and supply device connected to the flexible supply line 4, through the said flexible supply line 4 and through the coupling 11 to the hand piece 1. It has been found experimentally that a Er:YAG laser light having a wavelength of about 2.94 μm and a pulse duration of about 200 to 500 μs, preferably about 300 μs, is particularly suitable. Advantageous results are achieved with a pulse energy output of about 50 to 500 mJ. An associated laser generation device is preferably arranged so that the pulse energy can be varied and thus adjusted.

The first and/or the second light guides 5, 7 may be of a plastic material and/or glass or quartz. The coupling device is preferably arranged so that total reflection can occur. Total reflection is promoted if the first and/or second light guides 5, 7 consist of a core and a sleeve of materials of different angles of refraction, as is known per se.

We claim:

1. A medical or dental laser instrument (1) for tooth root canal treatments, including a rod-shaped handpiece (2), a connection part (3) for connecting the handpiece (2) to a supply line (4), a first light guide (5) extending longitudinally through the supply line (4) and the connection part (3) to the handpiece (2), a second light guide (7) located in a front end region of the laser instrument (1), and a coupling device (8) for coupling a laser light bundle extending from the first light guide (5) to the second light guide (7), the second light guide (7) having a cross-sectional size which is smaller than the cross-sectional size of the first light guide (5), characterized in that the second light guide (7) has a larger numerical aperture than the first light guide (5), a rear end of the second light guide (7) being arranged coaxially with the front end of the first light guide (5), said second light guide (7) being flexible and arranged in a supporting tube (26), the supporting tube (26) being located in a coaxial bore (24a) of a holding shank (23) from which the supporting tube (26) projects, the second light guide (7), the supporting tube (26) and the holding shank (23) conjointly forming a rigidly interconnected structural part (B), said supporting tube (26) having curved sides in a region projecting from the holding shank (23) with the flexible second light guide (7), the holding shank (23) being releasably connected to the handpiece (2) by a plug-in connection having a locking device (31), said holding shank (23) being insertable from the front thereof into a bore (22) formed in the handpiece (2), and the locking device having an annular groove (32) into which a locking element (33) is engageable under a biasing spring force.

2. A laser instrument according to claim 1, wherein the second light guide (7) has a cross-sectional size of about 200 μm to 500 μm and the first light guide (5) has a cross-sectional size of about 500 μm to 800 μm.

3. A laser instrument according to claim 1, wherein the numerical aperture of the second light guide (7) is larger than 0.2 and the numerical aperture of the first light guide (5) is smaller than 0.2.

4. A laser instrument according to claim 3, wherein the numerical aperture of the second light guide (7) is within the range of about 0.26 to 0.35 and the numerical aperture of the first light guide (5) is within the range of about 0.13 to 0.18.

5. A laser instrument according to claim 1, wherein the supporting tube (26) and the longitudinal center axis (28) of the laser instrument (1) subtend a forwardly opening acute angle (W).

6. A laser instrument according to claim 1, wherein the supporting tube (26) is made of plastically manually flexible metallic material.

7. A laser instrument according to claim 6, wherein said metallic material consists of steel.

8. A laser instrument according to claim 1, wherein the holding shank (23) is mounted on the handpiece (2) so as to be rotatable about the longitudinal center axis of the instrument.

9. A medical or dental laser instrument (1), for tooth root canal treatment, including a rod-shaped handpiece (2), a connection part (3) for connecting the handpiece (2) to a supply line (4), a first light guide (5) which extends longitudinally through the supply line (4) and the connection part (3) to the handpiece (2), a second light guide (7) arranged in a front end region of the laser instrument (1), and a coupling device (8) for coupling a laser light bundle extending from the first light guide (5) to the second light guide (7), a rear end of the second light guide (7) being arranged coaxially with a front end of the first light guide (5), the second light guide (7) being flexible and arranged in a supporting tube (26), the supporting tube (26) being located in a coaxial bore (24a) of a holding shank (23) having the supporting tube (26) projecting therefrom, the second light guide (7), the supporting tube (26) and the holding shank (23) conjointly forming a rigidly interconnected structural part (B), characterized in that the holding shank (23) is releasably connected to the handpiece (2) by a plug-in connection having a locking device (31), said holding shank (23) being forwardly insertable into a bore (22) formed in the handpiece (2), and the locking device having an annular groove (32) into which a locking device (33) engages under a biasing spring force.

10. A laser instrument according to claim 9, wherein the supporting tube (26) has curved sides in a region thereof projecting from the holding shank (23) with the flexible second light guide (7).

11. A laser instrument according to claim 1 or 9, wherein the holding shank (23) is rotatably mounted in the plug-in connection.

12. A laser instrument according to claim 1 or 9, wherein the locking device is manually depressable.

13. A laser instrument according to claim 1 or 9, wherein the annular groove (32) is formed in the holding shank (23).

14. A laser instrument according to claim 1 or 9, wherein the second light guide (7) projects forwardly from the supporting tube (26).

15. A laser instrument according to claim 1 or 9, wherein the holding shank (23) projects beyond the handpiece (2).

16. A laser instrument according to claim 1 or 9, wherein a lens (18) is arranged between the light guides (5, 7) at a distance (a, b) from respectively each of said light guides.

17. A laser instrument according to claim 1 or 9, wherein a plurality of structural parts (B) which vary with each other in the cross-sectional size of the light guide (7), in its length (L) projecting from the supporting tube (26), and/or in an angle (W) subtended with the longitudinal center axis (28) of the laser instrument.

* * * * *